(12) United States Patent
Baker et al.

(10) Patent No.: US 7,985,432 B2
(45) Date of Patent: Jul. 26, 2011

(54) INSECT REPELLENT

(75) Inventors: John D. Baker, Ontario (CA); John T. Arnason, Ottawa (CA); Calum McRae, Ontario (CA); Jose M. Wade, County Kildare (IE); Stanley J. Alkemade, Ontario (CA)

(73) Assignee: Bioniche Life Sciences, Inc., Belleville, Ontario (CA)

( * ) Notice: Subject to any disclaimer, the term of this patent is extended or adjusted under 35 U.S.C. 154(b) by 411 days.

(21) Appl. No.: 12/119,161

(22) Filed: May 12, 2008

(65) Prior Publication Data

US 2008/0213408 A1 Sep. 4, 2008

Related U.S. Application Data

(62) Division of application No. 10/851,774, filed on May 21, 2004, now Pat. No. 7,381,431.

(60) Provisional application No. 60/472,567, filed on May 22, 2003.

(51) Int. Cl.
A61K 36/00 (2006.01)

(52) U.S. Cl. .................................. 424/725; 424/728

(58) Field of Classification Search .................. None
See application file for complete search history.

(56) References Cited

U.S. PATENT DOCUMENTS

| 4,702,913 A | 10/1987 | Marty |
| 4,997,657 A | 3/1991 | Horrobin et al. |
| 5,061,720 A | 10/1991 | Walsh et al. |
| 5,352,700 A | 10/1994 | Frithz et al. |
| 5,639,460 A | 6/1997 | Raymond |
| 5,688,528 A | 11/1997 | Carlsson et al. |
| 5,859,057 A | 1/1999 | Schwartz et al. |
| 5,885,629 A | 3/1999 | Ford |
| 6,107,349 A | 8/2000 | Mantynen |
| 6,117,430 A | 9/2000 | Joseph |
| 6,242,012 B1 | 6/2001 | Schulick et al. |
| 6,361,806 B1 | 3/2002 | Allen |
| 6,365,197 B1 | 4/2002 | Shukla et al. |
| 6,365,656 B1 | 4/2002 | Green et al. |
| 6,413,555 B1 | 7/2002 | Lee |
| 6,414,036 B1 | 7/2002 | Ninkov |
| 6,432,429 B1 | 8/2002 | Maddern et al. |
| 6,451,356 B1 | 9/2002 | Shukla et al. |
| 6,482,446 B2 | 11/2002 | Watson |
| 6,485,756 B1 | 11/2002 | Aust et al. |
| 6,524,605 B1* | 2/2003 | Coats et al. .................. 424/408 |
| 6,551,625 B1 | 4/2003 | Hilaire et al. |
| 7,288,265 B1* | 10/2007 | Rolf .............................. 424/449 |
| 7,381,431 B2 | 6/2008 | Baker et al. |
| 2002/0107265 A1 | 8/2002 | Chen et al. |
| 2002/0150635 A1 | 10/2002 | Shukla et al. |
| 2003/0060379 A1 | 3/2003 | Souter et al. |
| 2003/0072828 A1 | 4/2003 | Harrison et al. |
| 2003/0096023 A1 | 5/2003 | Steck |
| 2003/0129213 A1 | 7/2003 | Gonzalez et al. |
| 2003/0129253 A1 | 7/2003 | Milley et al. |
| 2003/0138471 A1 | 7/2003 | Coats et al. |
| 2003/0194454 A1* | 10/2003 | Bessette et al. ............... 424/745 |
| 2003/0198659 A1 | 10/2003 | Hoffmann et al. |
| 2003/0235601 A1* | 12/2003 | Hallahan ....................... 424/405 |
| 2004/0024054 A1 | 2/2004 | Haenke |
| 2004/0033901 A1 | 2/2004 | Adamoli |
| 2005/0014730 A1* | 1/2005 | Carlson et al. ............... 514/169 |

FOREIGN PATENT DOCUMENTS

| CA | 2364556 A1 | 10/2000 |
| CA | 2182575 A1 | 11/2000 |
| CA | 2376517 A1 | 1/2001 |
| CA | 2382740 A1 | 3/2001 |
| DE | 20212185 U | 10/2002 |
| FR | 2 806 262 A1 | 9/2001 |
| JP | 09118629 A | 5/1997 |
| WO | WO 90/14824 A1 | 12/1990 |
| WO | WO 93/16594 A1 | 9/1993 |
| WO | WO 94/04029 A1 | 3/1994 |
| WO | WO 98/57542 A1 | 12/1998 |
| WO | WO 03/020232 A1 | 3/2003 |
| WO | WO 03/086069 A1 | 10/2003 |

OTHER PUBLICATIONS

Chris Peterson, et al., "Catnip Repels Mosquitoes More Effectivley Than DEET," Science Daily (www.sciencedaily.com/releases/2001/081010828075659.htm) and American Chemical Society (Aug. 28, 2001).
"Wellness Guide to Dietary Supplements: Evening Primrose Oil", UC Berkeley Wellness (www.berkeleywellness.com/html/ds/dsEveningPrimrose.php) (Mar. 1988).
Peterson et al., J. of Economic Entomology, 95(2) : 377-380 (Apr. 2002).
Peterson et al., J. of Economic Entomological Society of America, 96(4): 1275-1282 (2003).
Internet website: "Evening Primrose Oil: to help treat inflammatory disorders"; Vibrant Life; (Mar.-Apr. 2003) (4 pages total).
Australian Appln No. 2004241797, Examiners First Report issued Feb. 17, 2010.

(Continued)

*Primary Examiner* — Christopher R. Tate
(74) *Attorney, Agent, or Firm* — Kilpatrick Townsend & Stockton LLP

(57) ABSTRACT

The invention provides compositions and methods useful in repelling target pests, such as insects from target areas. The compositions comprise mixtures or solutions of at least one repellent composition. The compositions of the invention preferably include an effective amount of evening primrose oil ("EPO") to repel a target pest from a target area, such as animals, humans, plants or building structures, along with a carrier. The repellent composition may include a combination of EPO with another plant extract oil and a combination of EPO with catnip oil, optionally combined with another plant extract oil. The method for repelling target pests from animals comprises contacting a target area with the repellent composition to repel the target pest from the target area. The method also reduces transmission of infectious diseases transmitted by target pests by reducing contact of the pest with target areas.

31 Claims, 8 Drawing Sheets

OTHER PUBLICATIONS

Chinese Appln No. 2004800205951, First Office Action issued Apr. 13, 2007.
Chinese Appln No. 2004800205951, Second Office Action issued Aug. 28, 2009.
Chinese Appln No. 2004800205951, Notification to Grant Patent Right of Invention issued Feb. 12, 2010.
EPO Application No. 04734056.7, First Office Action issued Oct. 27, 2006.
EPO Application No. 04734056.7, Second Office Action issued May 3, 2007.
EPO Application No. 04734056.7, Communication under Rule 71(3) EPC: Intention to Grant a European Patent issued Apr. 28, 2008.

* cited by examiner

INSECT REPELLENT

PRIOR RELATED APPLICATIONS

The present application is a divisional application of U.S. patent application Ser. No. 10/851,774, filed May 21, 2004, now U.S. Pat. No. 7,381,431, which claims priority to U.S. Provisional Patent Application Ser. No. 60/472,567 filed on May 22, 2003, the entire contents of each are incorporated here by reference.

FIELD OF THE INVENTION

The invention relates to repellent compositions, and more particularly to repellent compositions that may be used to repel insects from animals, including humans, and also plants, soil, or building structures.

BACKGROUND OF THE INVENTION

Insects, particularly mosquitoes, carry diseases and are generally regarded as pests to both animals and plants. Every year, over one million people worldwide die from mosquito-borne diseases. Mosquitoes can carry many different kinds of diseases including malaria, heartworm, dengue fever, encephalitis, yellow fever and West Nile virus.

Because of the health concerns and discomfort related to insect bites and stings, insecticides, which kill insects, or repellents, which merely repel insects, are commonly used to keep insects away from animals, plants and building structures. However, commercially available insecticides, including those available for home use, commonly include active ingredients which are not only toxic to the target pests, but, if used in relatively confined environments and delivered as aerosol sprays, can be present in sufficient concentration to be toxic to humans and household pets. Various undesirable side effects may include immediate or delayed neurotoxic reactions and/or suffocation. Even the noxious odor of such materials can cause headaches or nausea in some individuals. These adverse side effects are exacerbated when such compositions come in contact with persons of increased sensitivity, or persons of small body mass such as children or babies.

Therefore, efforts have been made to develop insecticidal compositions, particularly those intended for residential use in aerosol form, which are effective in killing the targeted insect pests completely and quickly, but which are non-poisonous to humans and pets. Unfortunately, non-poisonous insecticidal compositions available heretofore have had limited efficacy. Attempts to use essential oils as the active ingredient in such insecticides, while having limited success, have generally been found to be either cost prohibitive, inadequately lethal to control a range of targeted insect pest species, or too slow-acting to enable the user to confirm that the insect has been killed and to dispose of the dead insect so as to avoid polluting the environment.

Furthermore, although insecticides, which kill the target pests, are usually the quickest forms of treatment, they kill not only the undesired insects, but beneficial insects as well. Therefore, insect repellents may be a compromise that minimizes disease and discomfort in animals and plants, without disrupting the natural balance of insects.

Accordingly, what is needed are new formulations useful for effectively repelling pests, including insects, from animals, plants and building structures. The formulations should be long lasting and of lesser toxicity than traditional repellents.

Additionally, effective repellents are needed to reduce the transmission of infectious disease. Because insects are also carriers of infectious diseases, a repellent composition the prevents or reduces the number of landings and bites of insects may reduce the transmission of infectious diseases.

SUMMARY OF THE INVENTION

The compositions and method of the present invention resolve many of the difficulties associated with conventional insect repellents described above. Through the invention, it has been determined that insects, particularly mosquitoes, may be more effectively repelled, with less risk to the environment and animals, through the use of plant extract essential oils. In particular, evening primrose oil ("EPO") has been found to be highly successful in repelling insects. Surprisingly, it has also been discovered that the combination of catnip oil, a known insect repellent, with EPO has a synergistic effect, resulting in greater than expected insect repellency. This synergistic effect is also seen when EPO and/or catnip oil is used in combination with N,N-diethyl-3-methylbenzamide ("DEET"). It has also been discovered that the combinations of EPO with other plant extract oils, and optionally including catnip oil, are effective insect repellents.

Compositions of the invention comprise mixtures of EPO and a carrier. Compositions of the invention also comprise mixtures or solutions of EPO, catnip oil and a carrier. Compositions of the invention further comprise mixtures of EPO and another plant extract oil, optionally combined with catnip oil.

In particular embodiments, the EPO is present in an amount between approximately 0.1% and 99% w/w. In other embodiments, the EPO is present in an amount between approximately 0.1% and 50% w/w. In additional embodiments, the EPO is present in an amount between approximately 1% and 10%. In preferred embodiments, the EPO is present in an amount between approximately 2% and 8% w/w.

In particular embodiments, the catnip oil is present in an amount between approximately 0.1% and 99% w/w. In other embodiments, the catnip oil is present in an amount between approximately 0.1% and 50% w/w. In additional embodiments, the catnip oil is present in an amount between approximately 1% and 10%. In preferred embodiments, the catnip oil is present in an amount between approximately 2% and 8% w/w.

These compositions of EPO, and EPO with catnip oil, further comprise one or more additional plant extract oils. The one or more additional plant extract oil may be allspice, anisum, basil, cajeput, catnip, cedar, chrysanthemum, cinnamon, citronella, clove, eucalyptus, garlic, geranium, lavender, marjoram, neem, pennyroyal, peppermint, pine, rosemary, sage, spearmint, thyme or any other members of the mint (Lamiaceae or Labiatae) family, tea-tree, vanilla or verbena or a combination thereof.

In certain embodiments, the one or more additional plant extract oil is present in an amount between approximately 0.1% and 99% w/w. In particular embodiments, the one or more additional plant extract oil is present in an amount between approximately 0.1% and 50% w/w. In still more particular embodiments, the one or more additional plant extract oil is present in amount between approximately 1% and 10% w/w. In preferred embodiments, the one or more additional plant extract oil is peppermint oil.

In certain embodiments, the compositions of the present invention further comprise DEET.

In other preferred embodiments, the compositions comprise an emulsifier, an anti-microbial agent and/or an antioxidant. In a more preferred embodiment, the emulsifier is lecithin.

The target pest may be a biting, sucking or chewing insect. The target pests include but are not limited to a mosquito, house fly, barn fly, face fly, bush fly, black fly, no see'um, deer fly, horse fly, beetle, gnat, tick, beer bug, flea, louse, bed bug, earwig, ant, cockroach, aphid, spruce bud worm, corn borer, sandflea, tsetse fly, mite or assassin bug.

The target area is at least one area on a human, animal, bird, plant, crop, tree, soil, field, greenhouse, barn, granary, home, deck, pool, commercial building, clothing, tent, shoe, boot, blanket, sleeping bag, backpack, table cloth or picnic table.

Embodiments of the invention are also directed to methods for reducing the incidence of an infectious disease caused by a target pest comprising applying the compositions to a target area. In a preferred embodiment of reducing the incidence of an infectious disease, the target area is at least one area on a human or an animal.

In certain embodiments of the invention, the infectious disease is an insect-borne disease. In particular embodiments, the infectious disease is any one of the following: malaria, yellow fever, dengue fever, West Nile encephalitis, Rift Valley fever, Arboviral Encephalitides, filariasis, babesiosis, ehrlichiosis, Lyme disease, Rocky Mountain spotted fever, Southern tick-associated rash illness, tick typhus, tularemia, encephalitis, Leishmaniasis, Carrion's disease, sand fly fever, African sleeping sickness, Chagas disease, lice infestation, epidemic relapsing fever, trench fever, typhus fever, onchoceriasis, tularemia, anthrax, loiasis, yaws, conjunctivitis, dysentery, cholera, poliomyelitis, bubonic plague and murine typhus.

In particular embodiments of the invention, the composition comprises evening primrose oil, catnip oil, a carrier, an emulsifier, an anti-microbial agent, and an antioxidant.

The invention includes methods for repelling a target pest from a target area comprising applying the composition to the target area.

Accordingly, it is an object of the invention to provide compositions for repelling pests, such as insects, from a target area.

Another object of the invention is to provide a method for repelling pests, such as insects, from a target area through application of the compositions of the present invention to a target area.

Yet another object of the invention is to provide a method of reducing the incidence of infectious disease through application of the compositions of the present invention to a target area.

These and other features and advantages of the present invention will become apparent after review of the following drawings and detailed description of the disclosed embodiments. Various modifications to the stated embodiments will be readily apparent to those of ordinary skill in the art, and the disclosure set forth herein may be applicable to other embodiments and applications without departing from the spirit and scope of the present invention.

BRIEF DESCRIPTION OF THE DRAWINGS

Specific embodiments of the invention are described below with reference to the drawings, which are described as follows.

DETAILED DESCRIPTION OF SPECIFIC EMBODIMENTS

Figure 1:
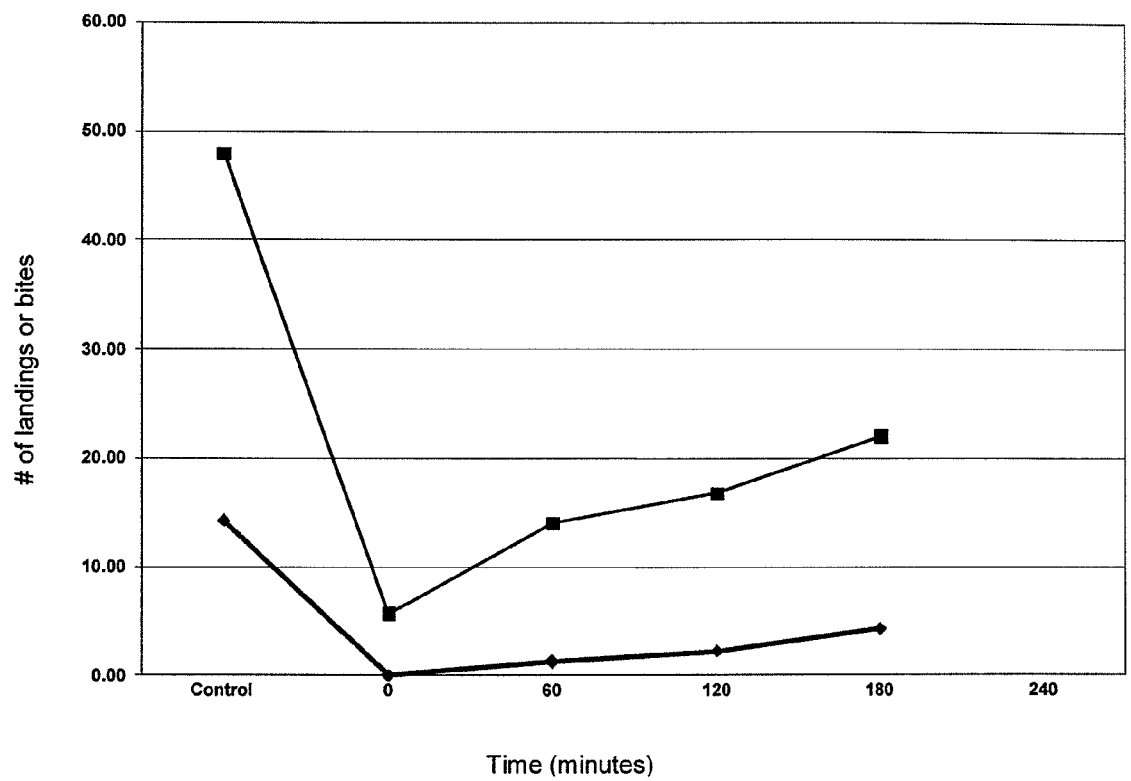
FIG. 1 is a chart showing the mean mosquito repellency provided by a combination of 2% catnip oil and 1% EPO. In this and subsequent figures, the Y-axis shows the number of landings or bites and the X-axis shows the time except for FIG. 4. In this and all subsequent figures except FIG. 8, the solid squares indicate mean landings and the solid diamonds indicate mean bites.

The invention relates to repellent compositions that are useful in repelling pests, such as insects, from target areas including but not limited to animals, including humans, clothing, plants and building structures. The repellent composition comprises evening primrose oil (EPO) and a carrier, EPO and catnip oil and a carrier, and either of these compositions in combination with a plant extract oil.

The term "repel," as used herein, means that less time (including no time) is spent in a target area than in a non-target area. Thus, to repel a target pest means deterring the pest from remaining in a target area. "Repel" may also include killing the target pest. "Repel" may also be used to refer to slowing the behavior and/or responsiveness of a target pest so that the presence of the target pest is less of a nuisance to the target area. "Repel" also includes minimizing the landings of the target pest on a target area, including entry of the target pests into building structures.

As used herein, target areas include, but are not limited to, areas on humans, animals, birds, plants, crops, trees, soils, fields, greenhouses, barns granaries, homes, decks, pools, commercial buildings, clothing, tents, shoes, boots, blankets, sleeping bags, backpacks, table cloths, picnic tables and the like. Animals include but are not limited to domestic animals, farm animals, wild animals, pets, and zoo animals.

As used herein, "target pest" generally includes, but is not limited to, biting, sucking and chewing insects. "Target pest" includes, but is not limited to, mosquitoes, flies (including house, barn, face, bush, and the like), black flies, no see'ums, deer flies, horse flies, beetles, gnats, ticks, beer bugs (raspberry beetles), fleas, lice, bed bugs, earwigs, ants, cockroaches, aphids, spruce bud worm, corn borers, sandfleas, tsetse flies, mites, assassin bugs and the like.

Repellent Compositions

Embodiments of the insect repellent include evening primrose oil (EPO). Evening primrose or *Oenothera biennis* (Onagraceae) is a genus of herbs and undershrubs distributed mainly in temperate America together with some species occurring in the tropics. The oil from seeds of *Oenothera biennis* is known to be a rich source of gamma-linolenic acid. EPO has surprisingly been found to be an effective pest repellent.

Embodiments of the repellent composition may include EPO and a carrier. The concentration of EPO in the repellent composition ranges from about 0.1% to about 99% by weight. Preferably, EPO is present in a concentration ranging from about 0.1% to about 50% by weight. More preferably, EPO is present in a concentration ranging from about 1% to about 10% by weight. More preferably, EPO is present in a concentration ranging from about 2% to about 8% by weight. In a preferred embodiment, EPO is present in a concentration of about 4% to about 6% by weight.

In another embodiment, the repellent composition includes EPO, a carrier and any of the plant extract essential oils selected from the following: allspice, anisum, basil, cajeput, catnip, cedar, chrysanthemum, cinnamon, citronella, clove, eucalyptus, garlic, geranium, lavender, marjoram, neem, pennyroyal, peppermint, pine, rosemary, sage, spearmint, thyme or any other members of the mint (Lamiaceae or Labiatae) family, tea-tree, vanilla, verbena or combinations thereof. The concentration of the additional plant extract essential oil(s) in the repellent composition ranges from about 0.1% to about 99% by weight. Preferably, the additional oil(s) are present in a concentration ranging from about 0.1% to about 50% by weight. More preferably, the additional oil(s) are present in a concentration ranging from about 1% to about 10% by weight. More preferably, the additional oil(s) are present in a concentration ranging from about 2% to about 8% by weight. In a preferred embodiment, EPO is present in a concentration of about 4% to about 6% by weight in combination with additional plant extract essential oil(s) present in a concentration of about 6% by weight.

Embodiments of the repellent composition comprising EPO and a carrier may also include any of the following essential oils, including but not limited to catnip oil, clove oil, peppermint oil, lavender oil or combinations thereof. The concentration of the additional essential oil ranges from about 0.1% to about 99% by weight. Preferably, the additional essential oil is present in a concentration ranging from about 0.1% to about 50% by weight. Preferably, the additional essential oil is present in a concentration ranging from about 1% to about 10% by weight. Preferably, the additional essential oil is present in a concentration ranging from about 2% to about 8% by weight. In a preferred embodiment, the additional essential oil is present in a concentration of about 4% to about 6% by weight.

In a preferred embodiment, the repellent compositions comprise catnip oil in combination with EPO. The concentration of the catnip oil ranges from about 0.1% to about 99% by weight. Preferably, the catnip oil is present in a concentration ranging from about 0.1% to about 50% by weight. Preferably, the catnip oil is present in a concentration ranging from about 1% to about 10% by weight. Preferably, the catnip oil is present in a concentration ranging from about 2% to about 8% by weight. In a preferred embodiment, the catnip oil is present in a concentration of about 4% to about 6% by weight. Catnip is the common name for a strong-scented perennial herb (*Nepeta cataria*) of the family Labiatae (mint family), native to Europe and Asia but naturalized in America. Catnip is best known for its stimulating effect on cats. Nepetalactone, the essential oil in catnip that gives the plant its characteristic odor, is about ten times more effective at repelling mosquitoes than DEET. Although *Nepeta cataria* was used in the present examples, it is to be understood that any of the more than 200 species of *Nepeta* may be used.

The following table 1 shows examples of the relative amounts (w/w) of active ingredients in the repellent composition of the invention. Any combination may be employed provided the combination of the relative amounts does not exceed 100%.

TABLE 1

| EPO | Catnip Oil | Optional Other (Non-Catnip) Essential Oils, including a combination thereof |
|---|---|---|
| 0.1-99% | 0.1-99% | 0.1-99% |
| 0.1-50% | 0.1-50% | 0.1-50% |
| 1-10% | 1-10% | 1-10% |
| 2-8% | 2-8% | 2-8% |
| 4-6% | 4-6% | 4-6% |

While not wishing to be bound by any theory, it is believed that EPO does not have repellency until it becomes oxidized on the target area, approximately one hour after application. It appears that the additional oils, such as catnip, clove, peppermint, lavender or any of the plant extract essential oils listed above, may provide repellency for at least the first hour until the EPO is oxidized. This beneficially extends the total period of repellency, requiring fewer reapplications. Thus, the repellent composition may include modified EPO and a carrier. The EPO may be modified such that it is oxidized prior to or immediately following application.

Another interesting property of the repellent composition is that when applied to skin, wetting of the skin may reactivate the composition such that the repellency is extended for an additional period of time. Thus, the repellency function may be extended by wetting the target area.

The repellent compositions of the present invention may also contain carriers, emulsifiers, or diluents as known to one of ordinary skill in the art. A carrier or diluent is an inert material used in making different formulations of the repellent compositions. The specific carrier used in any repellent composition depends on how the repellent composition will be applied (whether in a lotion, spray or dust form, for example) and where the repellent composition will be applied.

The repellent compositions optionally include anti-microbial agents to reduce the transfer of infectious diseases. As one with skill in the art will understand, any anti-microbial agents appropriate for application to the specific target area to be treated may be used.

The repellent compositions optionally include an antioxidant. The antioxidant assists in preventing rancidity of the oils and fats in the compositions. Although any suitable antioxidant may be used, rosemary extract has been found to be a suitable lipophilic antioxidant. As one with skill in the art will understand, any suitable antioxidant appropriate for application to the specific target area to be treated may be used.

The repellent compositions optionally include a fragrance that is not an insect attractant. Such fragrances are known to one of ordinary skill in the art.

Formulations

The repellent compositions may be formulated differently based on the target area (i.e., living vs. nonliving objects) and how the compositions are to be applied.

Spray formulations are known to one of ordinary skill in the art and include aqueous solutions, water-soluble powders, emulsifiable concentrates, water miscible liquids/powders (for compositions that are soluble in water), wettable powders or water-dispersible powders, flowable/sprayable suspensions or suspension concentrates, and oil solutions.

One spray formulation of the invention is an emulsifiable concentrate. In an emulsifiable concentrate, a concentrated organic solvent-based solution of the repellent composition (or the repellent composition alone if it is a liquid at room temperature) is added to an emulsifier. As used herein, an emulsifier is a detergent-like (surfactant) material that allows microscopically small oil droplets to be suspended in water to form an emulsion. The concentrate is thereby dispersed evenly throughout an aqueous solution and generally remains suspended for an extended period of time (in some cases for days).

Emulsifiers useful in the invention are generally known to one of ordinary skill in the art and include, but are not limited to the following: non-ionic or ionic polymers such as polyoxyethylenesorbitan monooleates (Tweens), such as Tween 20 and Tween 60; sorbitol (polysorbate 80); propylene glycol; polyethylene glycol; ethanol (ethyl alcohol); and methanol (methyl alcohol). Other surfactants that can be used as an emulsifier for pesticide formulations are the phosphate esters. Examples of commercially available phosphate ester surfactants include, but are not limited to the following: butyl phosphate; hexyl phosphate; 2-ethylhexyl phosphate; octyl phosphate; decyl phosphate; octyldecyl phosphate; mixed alkyl phosphate; hexyl polyphosphate; and octyl polyphosphate. Preferably, the emulsifier used is either plant extract, bees wax or commercial emsulfiers/surfactants such as Novomer EC-1, Ultrez 21, Pemulen TR-2NF, soaps, poloxamers, Tweens and the like). More preferably, a plant extract (e.g., plant lecithin, plant glycerin, plant waxes and glycoproteins) is used as the emulsifier if an emulsifiable concentrate of a repellent composition of the invention is to be formulated.

Wettable powders or water-dispersible powders are also an important spray formulation. Wettable powders are known to one of ordinary skill in the art and are made by mixing the repellent composition with a fine dust (generally clay or talc) and a wetting agent (a dry soap or detergent). This mixture is then dispersed in water before spraying. The wetting agent will act as an emulsifier in the aqueous solution and cause the otherwise insoluble repellent composition to dissolve in water. Emulsifiable concentrates are preferred over wettable powders for most applications because the wettable powder aqueous solution will tend to "settle" quickly and require agitation in order to keep a constant concentration of repellent composition while spraying.

Flowable/sprayable suspensions or suspension concentrates are another method of creating a spray formulation with a repellent composition that is insoluble in water. As used herein, a flowable/sprayable suspension is a suspension of very finely ground dust diluent and repellent composition in a non-solvent liquid (generally water). The suspension will then mix well with water and can be sprayed. Flowable/sprayable suspensions suffer the same disadvantage as wettable powders because they tend to "settle" out and give varying concentrations of repellent composition throughout spraying.

An oil solution is another method of creating a spray formulation with a repellent composition that is insoluble in water. Such oil solutions are known to one of ordinary skill in the art. The repellent composition is dispersed in oil and applied as an oil-based spray. This formulation is convenient for ready-to-use pesticides where further handling by the user is not desired.

Dust formulations are also known to one of ordinary skill in the art and can be utilized in formulations of the repellent compositions of the present invention. In a dust formulation, the repellent composition is mixed with a solid particulate diluent (preferably one with a size range of 50-100 μm). The dust formulation is then mixed with the air through the aid of a dusting machine. Although dust formulations have historically been the easiest to make and apply, application rates, and repellent composition concentrations have to be exceedingly high. Further, even though the amount of repellent composition applied is very high, the actual amount of the repellent composition that reaches the target is generally low because the dusts are prone to drift. Preferred diluents for use in dust formulations are silicon dioxide, zinc oxide, talc, diatomaceous earth, clays, calcium carbonate, wheat flour, and powdered nut hulls.

The repellent compositions of the invention can also be formulated into granular formulations as known to one of ordinary skill in the art. Granules, such as small pellets (usually 0.3-1.3 mm) of an inert carrier (usually clay), can be mixed with the repellent compositions to give the desired concentration. Granules can be formulated to allow a rapid release, or an extended release of the repellent composition over time. Granular formulations are useful for relatively small-scale (garden or houseplant) applications, and in applications where safer handling is desired.

The repellent compositions of the invention can also be formulated into aerosol formulations as known to one of ordinary skill in the art. In order to use an aerosol formulation, the repellent composition must be soluble in a pressurized, volatile, petroleum solvent. Upon application of the aerosol formulation, the solvent evaporates leaving micro-droplets of the repellent composition suspended in the air. Aerosol formulations are useful for indoor applications, or small-scale outdoor applications.

The repellent compositions of the invention can also be formulated into a lotion for topical application. The lotion compositions can be presented as a solution or a suspension of the repellent composition in a liquid medium.

The repellent compositions can also be combined with a sunscreen or tanning solution. The sunscreen or tanning solution may be of the usual formulations, such as a lotion, spray or aerosol.

Various formulations of the repellent composition may also be combined with an insecticide, such as DEET. Thus, the insecticide kills any insects that are not repelled by the repellent composition. Other acceptable insecticides for application to animals or humans, or to other target areas are commonly known to one of ordinary skill in the art and may be included in the compositions of the present invention. Due to the effective repellency of the repellent compositions, lower amounts of DEET are needed than are traditionally used. Embodiments of the repellent composition may include but are not limited to 0.1%-15% DEET, 1%-15% DEET or 2-15% DEET (w/w).

The repellent compositions may also include antimicrobial agents to further reduce the incidence of spreading infectious diseases.

Application

The formulated repellent composition can either be applied directly or can be diluted further before application. The diluent depends on the specific treatment to be accomplished, and the method of application. For example, a repellent composition that is to be applied to trees could be diluted further with water to make it easier and more efficient to spray with known spraying techniques. Sprays and lotions may be employed for application to skin or fur of humans or animals.

Repellent compositions, either diluted or undiluted, can be applied in a number of different ways. For small-scale application of a liquid repellent composition, backpack tanks, hand-held wands, spray bottles, or aerosol cans can be utilized. For somewhat larger scale application of liquid repellent compositions, tractor drawn rigs with booms, tractor drawn mist blowers, airplanes or helicopters equipped for spraying, or fogging sprayers can all be utilized. Small-scale application of solid formulations can be accomplished in a number of different ways, examples of which are: shaking product directly from the container or gravity-application by human powered fertilizer spreader. Large-scale application of solid formulations can be accomplished by gravity fed tractor drawn applicators, or similar devices.

Various formulations of the repellent compositions of the invention can be combined with slow-release systems including micro-beads, silicon-based formulas, encapsulation, etc. to extend the repellent time. The formulations can be so constituted that they release the active ingredient only or preferably in a particular location, possibly over a period of time (i.e., a sustained-release formulation). Such combinations provide yet a further mechanism for controlling release kinetics. The coatings, envelopes, and protective matrices may be made, for example, from polymeric substances or waxes and the pharmaceutically acceptable.

Repellent compositions of the invention may be applied as frequently as needed, based on the characteristics of the target area and the nature and concentration of the target pests to be repelled.

Reduction of Disease Transmission

Embodiments of the repellent composition of the invention may also be used to reduce disease transmission. For example, embodiments of the repellent composition may be used to reduce the incidence of common insect-borne diseases of humans and other animals. Following are some common examples of insect-borne diseases. Mosquitoes may be vectors for malaria, yellow fever, dengue fever, and West Nile encephalitis, Rift Valley fever, Arboviral Encephalitides, such as Eastern equine encephalitis, Japanese encephalitis, La Crosse encephalitis, St. Louis encephalitis, West Nile virus and Western equine encephalitis, and filariasis. Ticks can be vectors for babesiosis, ehrlichiosis, Lyme disease, Rocky Mountain spotted fever, Southern tick-associated rash illness, tick typhus, tularemia and encephalitis. Sand fleas are vectors for Leishmaniasis, Carrion's disease and sand fly fever. Tsetse flies can be vectors for African sleeping sickness. Assassin bugs may be vectors for Chagas disease. Lice may be vectors for lice infestation, epidemic relapsing fever, trench fever and typhus fever. Black flies may be vectors for filariasis and onchoceriasis. Horse flies and deer flies may be vectors for tularemia, anthrax and loiasis. Eye gnats can be vectors for yaws and conjunctivitis. House flies may be vectors for dysentery, typhoid fever, cholera and poliomyelitis. Rat fleas are carriers of bubonic plague and murine typhus. In addition, various parasitic, rickettsial, bacterial and viral diseases of animals and man are spread by mosquitoes, ticks, biting flies, fleas, lice and other biting insects. Application of the repellent composition of the invention reduces the incidence of the diseases in humans and animals by reducing the number of insect bites.

The following examples will serve to further illustrate the present invention without, at the same time, however, constituting any limitation thereof. On the contrary, it is to be clearly understood that that resort may be had to various other embodiments, modifications and equivalents thereof which, after reading the description herein, may suggest themselves to those skilled in the art without departing from the spirit and scope of the invention.

Example 1

Administration of the Repellent Composition Reduces Mosquito Landings and Bites in Humans A laboratory culture of *Aedes atropalpus* adults maintained in continuous culture at the University of Ottawa was used. The culture was derived from collections made from temporary pools in shale beds along the Ottawa River at Fitzroy Harbour, Ontario. This species is known as the rock hole breeding mosquito and is found in southern Ontario and Quebec. It is representative of the many *Aedes* spp. which are the most important mosquitoes biting humans in spring and summer. The genus is capable of transmitting tropical diseases such as dengue and yellow fever. This species of mosquito is a known vector that transmits West Nile virus.

The WHO test protocol for mosquito repellents was used (Barnard, D. R. 2000. Repellent and toxicants for personal protection. WHO/CDS/WHOPES). Two clear Perspex™ mosquito cages (38 cm×38 cm×38 cm) containing more than 400 adults of both sexes and various ages were used. The investigators wore gloves to protect hands and introduced their forearms up to the elbow through a cloth sleeve entry port into the cage. For the controls, an untreated arm was exposed for 3-minute period. The number of landings and bites were recorded as bites per 3-minute period. Subsequently each forearm was treated (1 ml of repellent per forearm) with a different repellent and each forearm was introduced into the cages for a further 3 minutes of evaluation. After one hour, the forearms were exposed a second time and landings and bites recorded. This procedure was repeated at hourly intervals, collecting data until the product failed to protect against bites. Failure occurred when there were two bites within the 3-minute test period. The two principal investigators volunteered along with 2 male subjects in their mid 20's.

The compounds tested contained various levels of catnip (*Nepeta cataria*) essential oil, and evening primrose (*Oenothera biennis*) high gamma linoleic acid ("GLA") vegetable oil. A formulation with active ingredient, steam distilled catnip oil (80% nepetalactone), and a second active ingredient, cold pressed evening primrose oil (10% GLA) was prepared as an emulsifiable concentrate in water, using Novemer EC-1 (Noveon Inc., Cleveland, Ohio) distributed by L.V. Lomas Ltd. Bampton, Ontario. The formulation contained 8.0 g/L of Novemer EC-1 emulsifying agent, plus 1.0 g/L of rosemary extract (lipid antioxidant), and 3.0 g/L of Germall Plus (topical antimicrobial agent). The active ingredients (catnip oil and evening primrose oil) were varied and tested as follows: (1) 2% Catnip+1% EPO; (2) 4% Catnip+1% EPO; (3) 8% Catnip+1% EPO; (4a) 1% EPO; (4b) 2% EPO; (4c) 4% EPO; (4d) 8% EPO; and (5) 4% Catnip+4% EPO.

The mosquitoes were attracted to, landed on, probed and promptly took blood meals from the unprotected human forearms. After the application of the repellent, the mosquitoes clearly avoided the forearms in their flight behavior. Catnip oil concentrations less than 1% (data not presented) provided low protection.

Figure 2:
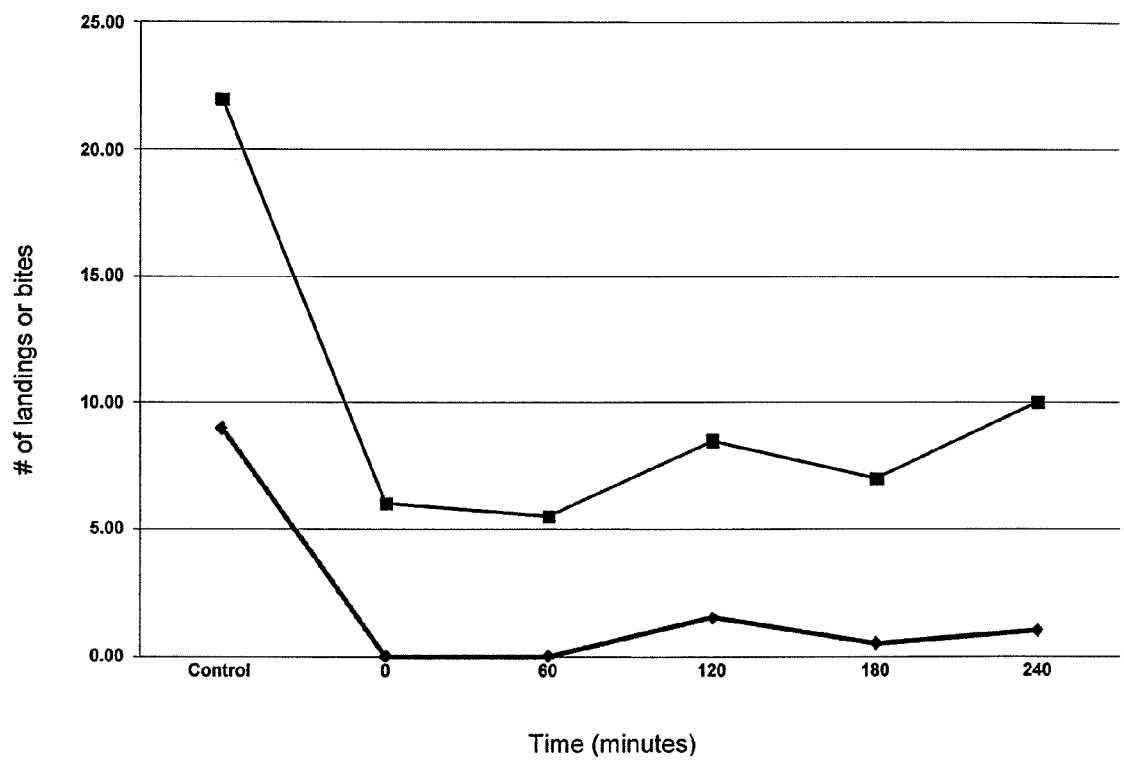
FIG. 2 is a chart showing the mean mosquito repellency provided by a combination of 4% catnip oil and 1% EPO.
Figure 3:
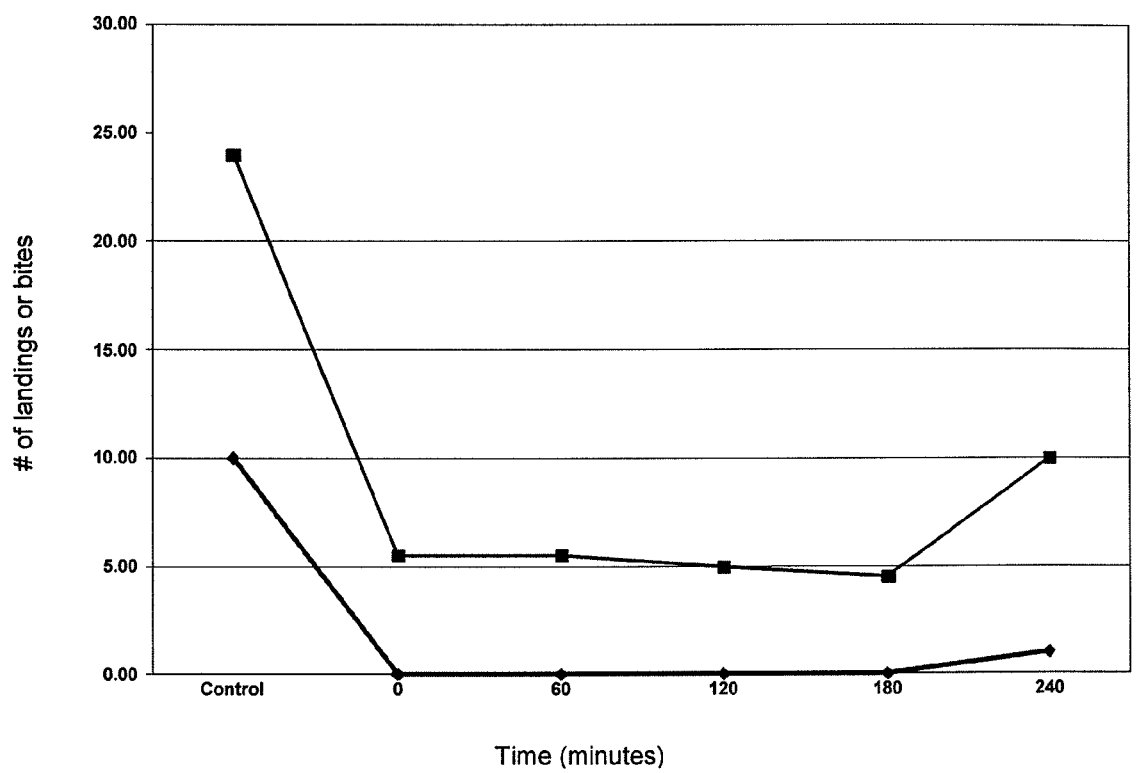
FIG. 3 is a chart showing the mean mosquito repellency provided by a combination of 8% catnip oil and 1% EPO.

As shown in FIG. 1, 2% catnip oil and 1% EPO provided about 1 hour of protection. After 60 minutes there appeared to be a gradual loss in efficacy, as both landings and bites increased. The mixture of 4% catnip oil and 1% EPO showed fewer bites and landings over a longer period of time (FIG. 2). Eight percent catnip oil and 1% EPO demonstrated no bites for 3 hours and greatly reduced landings (FIG. 3). However, the benefits over the 4% product were not significant.

Figure 4:
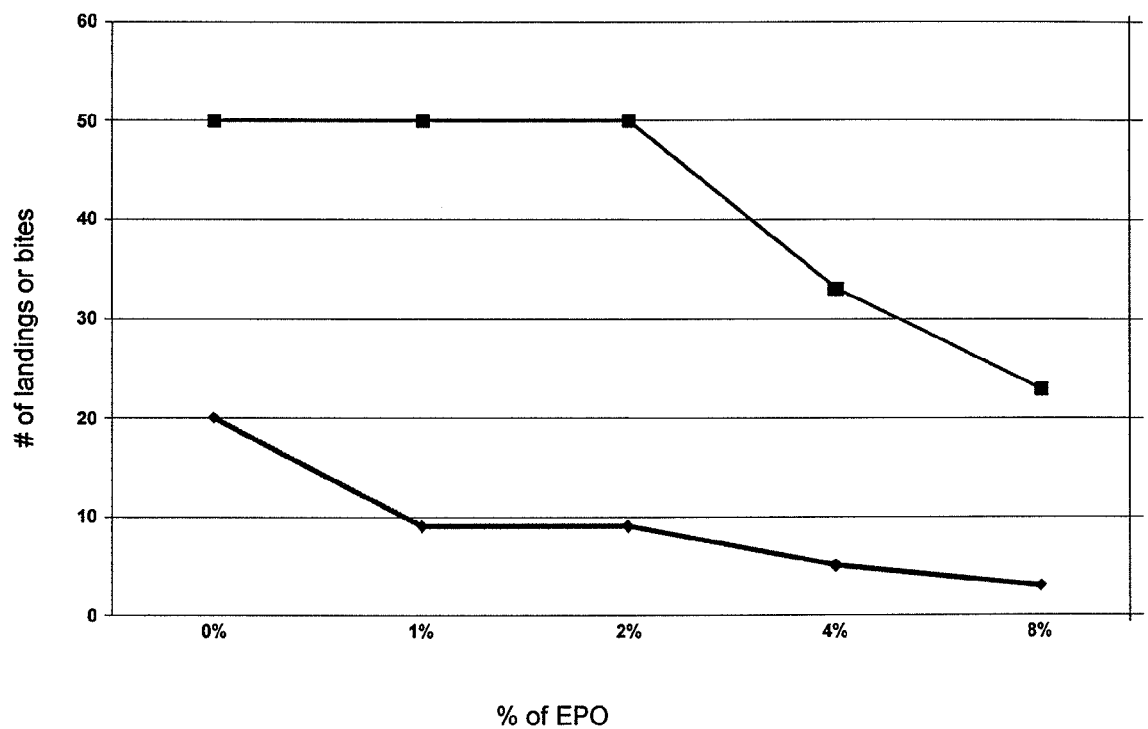
FIG. 4 is a chart showing the mean mosquito repellency provided by EPO alone at different concentrations of EPO.
Figure 5:
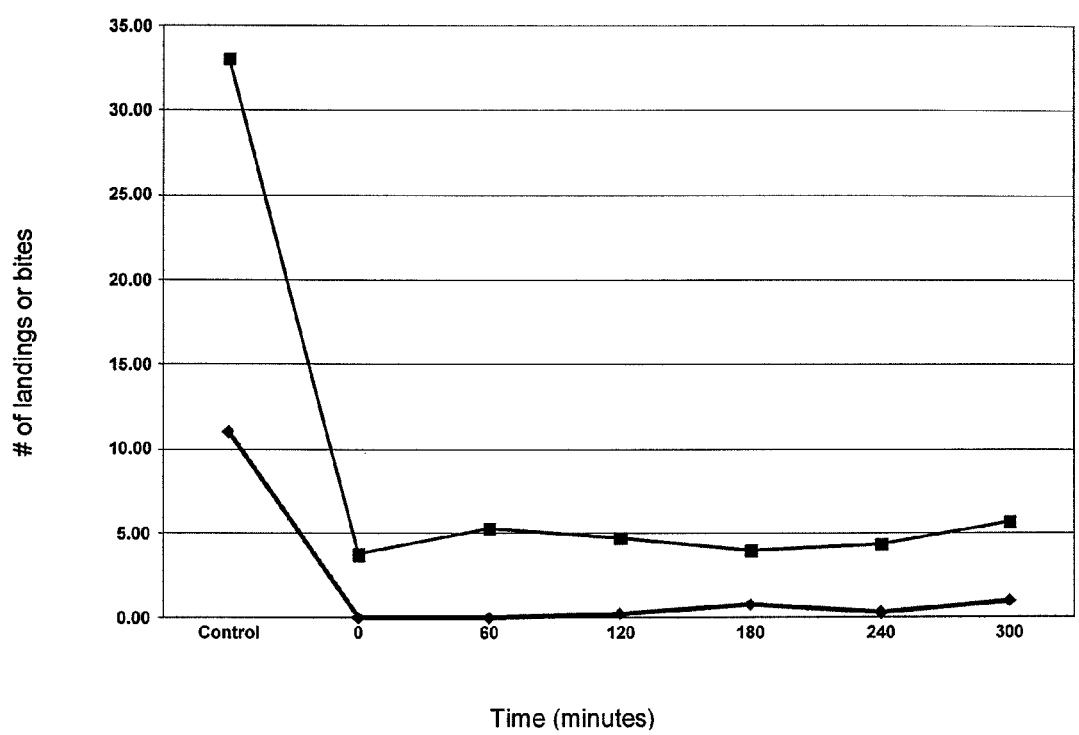
FIG. 5 is a chart showing the mean mosquito repellency of a combination of 4% catnip oil and 4% EPO.

Evening primrose alone had some repellency, but formulations needed to contain levels of EPO greater than 2% to see reductions in both landings and bites (FIG. 4). The combination of 4% catnip and 4% EPO provided up to 4 hours of protection (FIG. 5).

The 4% EPO contributed to a more sustained release, effective product that seemed to perform better than the catnip alone. EPO is a well-recognized essential fatty acid topical skin agent and makes the product feel very smooth upon application as a lotion to the skin. Individuals receiving EPO reported that the product had a pleasant odor (between sage and mint). The odor is softened somewhat when the evening primrose level was raised to 4%.

The complete data set for the product containing 4% catnip oil and 4% EPO can be found in Table 2. The data from Table 2 is graphically presented in FIG. 5. Table 2 shows the number of landings and bites in a 3-minute test period.

TABLE 2

| Volunteer | | #1 | | #2 | | | | | | |
|---|---|---|---|---|---|---|---|---|---|---|
| Catnip | | 4% | 4% | 4% | 4% | | | | | |
| EPO | | 4% | 4% | 4% | 4% | | | | | |
| | | Left Landings/ Bites | Right Landings/ Bites | Left Landings/ Bites | Right Landings/ Bites | n | Landings mean | s | Bites mean | s |
| Control | hr | 16 (10) | 16 (10) | 50 (12) | 50 (12) | 4 | 33.00 | 17.00 | 11.00 | 1.150 |
| t = 0 min | 0 | 4 (0) | 7 (0) | 1 (0) | 3 (0) | 4 | 3.75 | 2.50 | 0.00 | 0.000 |
| t = +60 min | 1 | 12 (0) | 5 (0) | 0 (0) | 4 (0) | 4 | 5.25 | 4.99 | 0.00 | 0.000 |
| t = +120 min | 2 | 6 (0) | 8 (1) | 2 (0) | 3 (0) | 4 | 4.75 | 2.75 | 0.25 | 0.500 |
| t = +180 min | 3 | 7 (2) | 9 (1) | 0 (0) | 0 (0) | 4 | 4.00 | 4.69 | 0.75 | 0.960 |
| t = +240 min | 4 | | 9 (0) | 1 (0) | 3 (1) | 3 | 4.33 | 4.93 | 0.33 | 0.570 |
| t = +300 min | 5 | | 12 (2) | 2 (0) | 3 (1) | 3 | 5.66 | 6.67 | 1.00 | 1.160 |

The product was an effective repellent in this test at a concentration of 2% of the active ingredient or greater. It compares favorably with other essential oils tested using this procedure. When the level of the catnip oil was elevated to 4% and the emulsion was combined with the 4% evening primrose oil, the product provided sustained protection for a period of 3 to 5 hours or longer for some individuals.

Example 2

A Combination of EPO and Catnip Oil Provides Greater Repellency than Catnip Alone The laboratory culture of *Aedes atropalpus* adults described in Example 1 was used. The procedure described in Example 1 was repeated.

The compounds tested contained 4% of catnip (*Nepeta cataria*) essential oil, and either 4% or 0% evening primrose (*Oenothera biennis*) high gamma linoleic acid ("GLA") vegetable oil. A formulation with active ingredient steam distilled catnip oil (80% nepetalactone), and a second active ingredient cold pressed evening primrose oil (10% GLA) was prepared as an emulsifiable concentrate in water, using Novemer EC-1 (Noveon Inc., Cleveland, Ohio) distributed by L.V. Lomas Ltd. Bampton, Ontario. The formulation contained 8.0 g/L of Novemer EC-1 emulsifying agent, plus 1.0 g/L of rosemary extract (lipid antioxidant), and 3.0 g/L of Germall Plus (topical antimicrobial agent). The active ingredients (catnip oil and evening primrose oil) tested were 4% catnip+ 4% EPO and 4% catnip+0% EPO.

The mosquitoes were attracted to, landed on, probed and promptly took blood meals from the unprotected human forearms. After the application of the repellent, the mosquitoes clearly avoided the forearms in their flight behavior. A combination of catnip oil and EPO provided greater protection than catnip oil alone.

Figure 6:
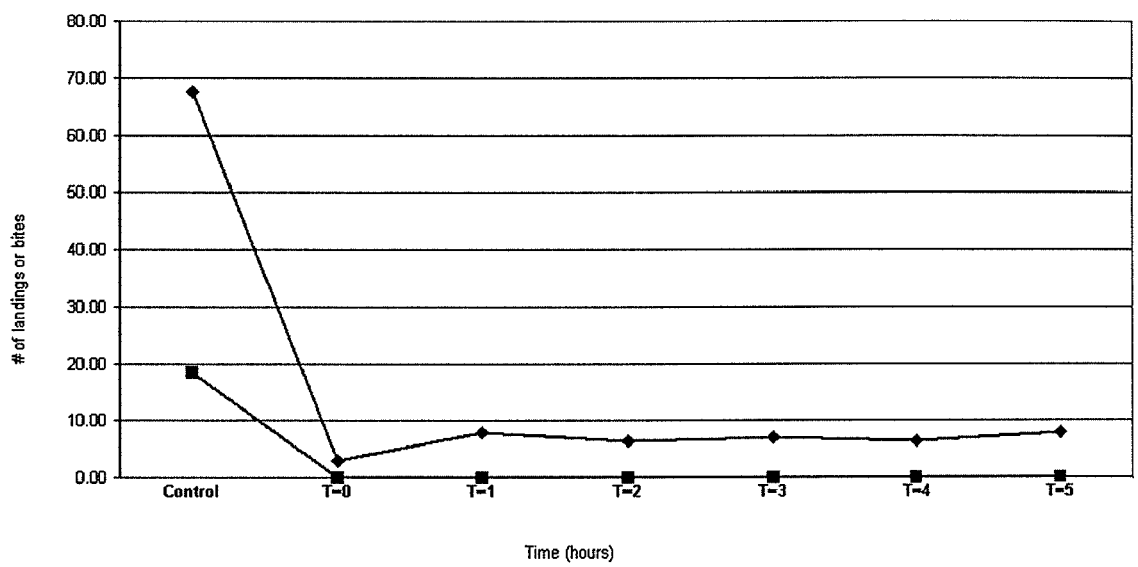
FIG. 6 is a chart showing the mean mosquito repellency of a combination of 4% catnip oil and 4% EPO.

FIG. 6 shows the mean efficacy of the 4% catnip oil and 4% EPO. It appears from this data that the product is provided up to 4 hours of protection.

The complete data set for the product containing 4% catnip oil and 4% EPO is shown in Table 3. The data from Table 3 is graphically presented in FIG. 6. Table 3 shows the number of landings and bites in a 3 minute test period.

TABLE 3

| | Vol. # | | | | | | | | Statistics | | | |
|---|---|---|---|---|---|---|---|---|---|---|---|---|
| | 1 | | | | 2 | | | | | | | |
| Time | Left | | Right | | Left | | Right | | Landings | | Bites | |
| (hr) | Landings | Bites | Landings | Bites | Landings | Bites | Landings | Bites | Mean | SD | Mean | SD |
| Control | 75 | 32 | 75 | 32 | 60 | 5 | 60 | 5 | 67.50 | 8.66 | 18.50 | 15.59 |
| T = 0 | 3 | 0 | 1 | 0 | 3 | 0 | 8 | 0 | 3.00 | 2.99 | 0.00 | 0.00 |
| T = 1 | 6 | 0 | 8 | 0 | 11 | 0 | 8 | 1 | 8.00 | 2.06 | 0.00 | 0.50 |
| T = 2 | 6 | 0 | 4 | 0 | 13 | 0 | 7 | 0 | 6.50 | 3.87 | 0.00 | 0.00 |
| T = 3 | 3 | 1 | 5 | 0 | 11 | 0 | 9 | 0 | 7.00 | 3.65 | 0.00 | 0.50 |
| T = 4 | 2 | 0 | 6 | 0 | 13 | 0 | 7 | 0 | 6.50 | 4.55 | 0.00 | 0.00 |
| T = 5 | 4 | 0 | 8 | 0 | 13 | 1 | 8 | 0 | 8.00 | 3.69 | 0.00 | 0.50 |

Figure 7:
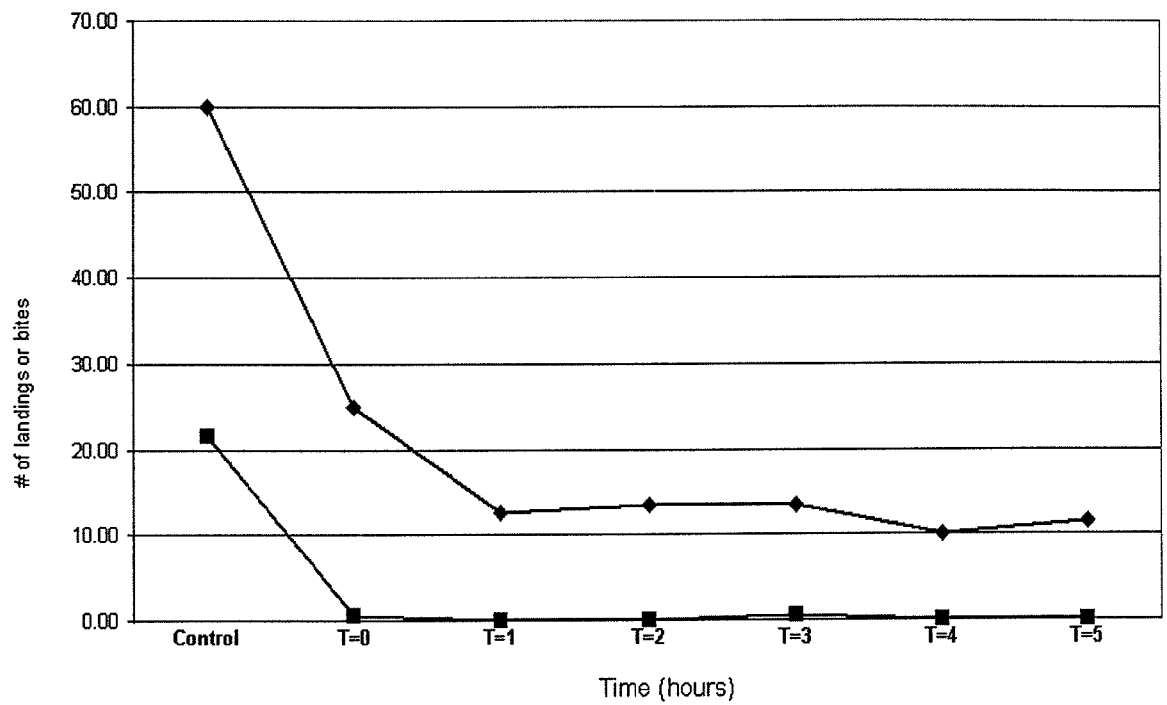
FIG. 7 is a chart showing the mean mosquito repellency of a combination of 4% catnip oil and 0% EPO.

FIG. 7 demonstrates that catnip oil alone has some repellency, but formulations need to contain EPO to cause reductions in both landings and bites.

The complete data set for the product containing 4% catnip oil and 0% EPO can be found in Table 4. The data from Table 4 is graphically presented in FIG. 7. Table 4 shows the number of landings and bites in a 3 minute test period.

TABLE 4

| Time (hr) | Vol. # 3 Left Landings | Vol. # 3 Left Bites | Vol. # 3 Right Landings | Vol. # 3 Right Bites | Vol. # 4 Left Landings | Vol. # 4 Left Bites | Vol. # 4 Right Landings | Vol. # 4 Right Bites | Statistics Landings Mean | Statistics Landings SD | Statistics Bites Mean | Statistics Bites SD |
|---|---|---|---|---|---|---|---|---|---|---|---|---|
| Control | 60 | 20 | 60 | 20 | 60 | 23 | 60 | 23 | 60.00 | 0.00 | 21.50 | 1.73 |
| T = 0 | 40 | 2 | 30 | 0 | 20 | 1 | 12 | 0 | 25.00 | 12.15 | 0.50 | 0.96 |
| T = 1 | 16 | 3 | 20 | 0 | 5 | 0 | 9 | 0 | 12.50 | 6.76 | 0.00 | 1.50 |
| T = 2 | 15 | 0 | 17 | 0 | 8 | 0 | 12 | 1 | 13.50 | 3.92 | 0.00 | 0.50 |
| T = 3 | 17 | 1 | 21 | 2 | 10 | 0 | 6 | 0 | 13.50 | 6.76 | 0.50 | 0.96 |
| T = 4 | 15 | 0 | 12 | 1 | 8 | 0 | 6 | 0 | 10.00 | 4.03 | 0.00 | 0.50 |
| T = 5 | 24 | 3 | 15 | 0 | 7 | 0 | 8 | 0 | 11.50 | 7.85 | 0.00 | 1.50 |

The product was an effective repellent in this test when a combination of catnip oil and EPO is used. The combination of catnip oil and EPO had greater repellency than catnip oil alone. A 4% catnip oil/4% EPO emulsion provided 3 to 5 hours of repellent efficacy.

Example 3

Administration of the Repellent Composition Reduces Insect Landings and Bites in Horses Ten horses from local farms were used. The horses were commonly found on farms in Canada. The repellent composition tested contained 4% catnip (*Nepeta cataria*) essential oil and 4% evening primrose (*Oenothera biennis*) high GLA vegetable oil. Otherwise, the composition was as described in Example 1.

The horses were kept in a pasture near a pond in Canada. The experiment was performed during the summer when mosquitoes are more prevalent. Each of the horses was treated by its owner with 25 ml of the repellent composition on the right side of its neck. Thus, each animal acted as its own control and different rates of carbon dioxide release did not interfere with the results. The horses were allowed to graze and move about as they normally do. After one-half hour, the horses were evaluated for bites and then allowed to continue grazing. This procedure was repeated every half hour for three hours.

Mosquitoes were more attracted to and took more blood meals from the unprotected left sides of the necks of the horses. The right sides of the horses' necks, which were treated with the repellent composition, were avoided by the mosquitoes. The repellent composition provided repellency for approximately two hours based on reports from the horse owners. In addition, there were very strong indications that the 4% EPO/4% Catnip composition provided excellent repellency for horse flies and deer flies. The observation by all owners was that it provided exceptional control for these pests particularly during competition/performance events where these biting insects are a great distraction and irritant to the horse.

Example 4

Water Reactivates the Repellent Composition when Applied to Horses

The purpose of this experiment was to determine whether water reactivates the repellency of the repellent composition after five hours. A few of the horses from Example 3 were wetted down with water from a common garden hose.

The horses were allowed to graze and move about as they normally do. After one-half hour, the horses were evaluated for additional bites and then allowed to continue grazing. This procedure was repeated every half hour for two hours.

Watering the surface treated with the repellent composition effectively reactivated the composition such that it continued repelling mosquitoes for a period of time. Mosquitoes were deterred from taking blood meals from the areas that were originally treated and were rewetted. The reactivated repellent composition provided repellency for at least an additional hour.

Example 5

Water Reactivates the Repellent Composition when Applied to Humans

The laboratory culture of *Aedes atropalpus* adults described in Example 1 was used. The procedure described in Example 1 was repeated.

When the product failed to protect against bites, the forearms were wetted by dipping in water. Thereafter, the procedure of 3-minute exposure was continued every hour, collecting data until the product again failed to protect against bites.

The repellent composition contained 4% catnip (*Nepeta cataria*) essential oil and 4% evening primrose (*Oenothera biennis*) high GLA vegetable oil. Otherwise, the composition was as described in Example 1.

The mosquitoes were attracted to, landed on, probe and promptly took blood meals from the unprotected human forearms. After the application of the repellent, the mosquitoes clearly avoided the forearms in their flight behavior. Although the repellent composition failed to protect the forearms after approximately 3 to 5 hours, the repellency was reactivated by exposure to water. After wetting the forearms, the mosquitoes again avoided the forearms in their flight behavior.

The product provides additional sustained protection beyond the original period of 3 to 5 hours. The repellency of the product appeared to be extended or reactivated by exposure to water.

Example 6

Water Reactivates the Repellent Composition when Applied to Humans

The laboratory culture of *Aedes aegypti* adults described in Example 1 was used. The procedure described in Example 1 was repeated.

When the product failed to protect against bites, the forearms were wetted by dipping in water. Thereafter, the procedure of 3-minute exposure was continued every hour, collecting data until the product again failed to protect against bites.

The repellent compositions tested contained 4%, 6% or 8% catnip (*Nepeta cataria*) essential oil and 4% evening primrose (*Oenothera biennis*) high GLA vegetable oil. The composition was as described in Example 1 with one exception. A repellent composition with 6% catnip oil and 4% evening primrose high GLA vegetable oil was prepared as described in Example 1, but Ultrez 21 emulsifying agent (Noveon Inc., Cleveland, Ohio) was added as the emulsifying agent and 2% peppermint oil was added for fragrance.

Figure 8:
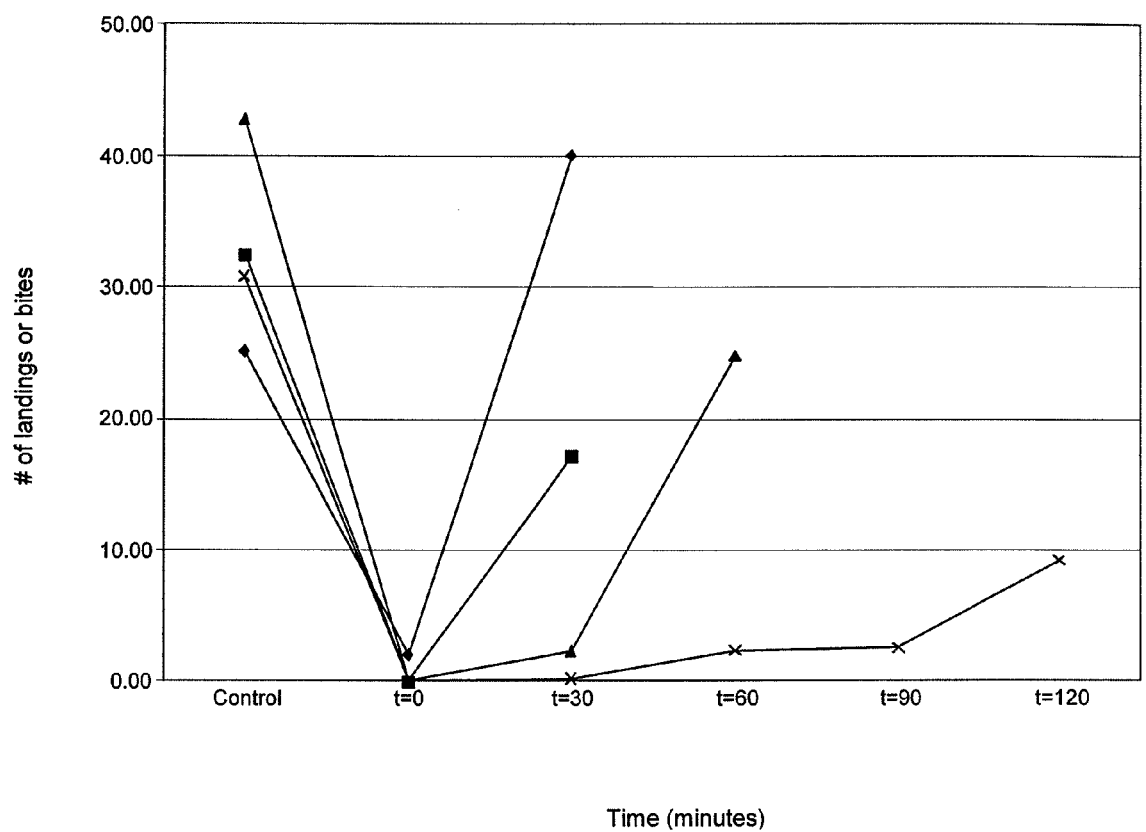
FIG. 8 is a chart showing the mean mosquito repellency of a combination of 4% EPO and 4%, 6% or 8% catnip oil. The solid diamonds indicate 4% EPO and 4% catnip oil administered in May 2003. The solid squares indicate 4% EPO and 6% catnip oil administered in May 2003. The solid triangles indicate 4% EPO and 8% catnip oil administered in May 2003. The Xs indicated 4% EPO and 8% catnip oil administered in August 2003.

The mosquitoes were attracted to, landed on, probed and promptly took blood meals from the unprotected human forearms. After the application of the repellent, the mosquitoes clearly avoided the forearms in their flight behavior. The repellent composition protected the forearms for approximately 0.5 to 2.0 hours, depending on the concentration of catnip oil. A summary of the results can be seen in FIG. 8.

*Aedes aegypti* is a much more aggressive strain of mosquito and an evaluation of the performance of various formulations of the repellent was suggested. The product provides protection against even aggressive mosquito strains such as *A. aegypti*. The repellency of the product appears to be extended or reactivated by exposure to water.

Example 7

The Repellent Composition is Effective in Repelling Horse Flies and Deer Flies from Humans

Deer flies (*Chrysops* species) and horse flies (*Chrysops* species) were used. The repellent was tested by five human subject volunteers that worked either outdoors or in recreational fields (hiking, riding, gardening and walks) in areas of large numbers of deer flies and/or horse flies. The conditions were sunny, hot and dry and the insect pressures in some cases were unbearable for humans.

The volunteers applied the product with approximately 2 mL of repellent composition per exposed arm. The product was also applied to all exposed areas including the head (face, neck, hair) and legs. The volunteers then went about their normal activities, and were later consulted about the effectiveness of the product.

The repellent composition tested was an emulsion of 4% EPO (*Oenothera biennis*) and 4% catnip (*Nepeta cataria*) oil. Otherwise the composition was prepared as described in Example 1.

The subjects reported that prior to the application of the test repellent, the horse flies and deer flies were present in high numbers, and were aggressive and persistent in their attacks. The flies circled, buzzed, landed and bit the subjects. After the application of the repellent, the deer flies and horse flies were visibly present and hovered around the subjects but did not come closer than approximately 0.5 meters. For a period of up to 2 hours after the application of the repellent, there were no fly landings or bites. The repellent composition was an effective repellent against deer flies and horse flies in human subjects.

Example 8

The Repellent Composition is Effective in Repelling Horse Flies and Deer Flies from Horses

Deer flies (*Chrysops* species) and horse flies (*Chrysops* species) were used. The repellent composition was provided to the owners of six show horses that compete at regional, provincial and national horse shows in Canada. The owners applied the repellent composition to their horses during daytime for training sessions and at competitions in late July and early August. The training and the competition occurred in areas having high deer fly and horse fly pressure, usually in conditions that were hot and dry. In some cases, the insect pressure was almost unbearable for both the riders and the horses.

The owners applied the test repellent at a normal rate as described in Example 3, but to vulnerable areas such as the head, belly, loins and legs. The owners/riders went about their normal activities (training, riding, competing), and were later consulted about the effectiveness of the product on the horses.

The repellent composition tested was an emulsion of 4% evening primrose oil (*Oenothera biennis*) and 4% catnip oil (*Nepeta cataria*). Otherwise the composition was prepared as described in Example 1.

The horse owners reported that prior to the application of the test repellent both the horse flies and deer flies were present in high numbers and were aggressive with persistent attacks characterized by circling, buzzing, landing and biting. This made the horses uneasy and difficult to control. Untreated horses exhibited irritable behavior, such as shaking heads, swishing tails, shaking whole body, twitching skin, leg movement to kick at flies, stomping of feet, and turning of the heads to bite at the flies. However, after the application of the repellent composition, no landings or bites by the flies occurred for approximately 1-2 hours. The flies were still present and hovered around the horses, but did not land on the horses. The horses were observed to be in a more relaxed state and able to concentrate, and carry out commands given by their riders. The repellent composition was an effective repellent against deer flies and horse flies in horses.

All patents, publications and abstracts cited above are incorporated herein by reference in their entirety. The foregoing description is provided for describing various embodiments and structures relating to the invention. Various modifications, additions and deletions may be made to these embodiments and/or structures without departing from the scope and spirit of the invention.

What is claimed is:

1. A method for reducing the incidence of disease transmission by a target pest comprising administering a composition comprising evening primrose oil, catnip oil and a carrier to a target area, wherein the composition retards contact of the target pest with the target area, and wherein the evening primrose oil is present in an amount between approximately 2% and 8% w/w and the catnip oil is present in an amount between approximately 2% and 8% w/w.

2. The method of claim 1, wherein the target pest is a biting, sucking or chewing insect.

3. The method of claim 1, wherein the target pest is a mosquito, house fly, barn fly, face fly, bush fly, black fly, no see'um, deer fly, horse fly, beetle, gnat, tick, beer bug, flea, louse, bed bug, earwig, ant, cockroach, aphid, spruce bud worm, corn borer, sandflea, tsetse fly, mite or assassin bug.

4. The method of claim 1, wherein the target area is at least one area on a human, animal, bird, plant, crop, tree, soil, field, greenhouse, barn, granary, home, deck, pool, commercial building, clothing, tent, shoe, boot, blanket, sleeping bag, backpack, table cloth or picnic table.

5. The method of claim 1, wherein the target area is at least one area on a human or an animal.

6. The method of claim 1, wherein the composition further comprises one or more additional plant extract oils, wherein the one or more additional plant extract oil is allspice, anisum, basil, cajeput, cedar, chrysanthemum, cinnamon, citronella, clove, eucalyptus, garlic, geranium, lavender, marjoram, neem, pennyroyal, peppermint, pine, rosemary, sage, spearmint, thyme or any other members of the mint (Lamiaceae or Labiatae) family, tea-tree, vanilla, verbena or a combination thereof.

7. The method of claim 6, wherein the one or more additional plant extract oil is present in an amount between approximately 0.1% and 50% w/w.

8. The method of claim 6, wherein the one or more additional plant extract oil is present in an amount between approximately 1% and 10% w/w.

9. The method of claim 1, wherein the composition further comprises DEET.

10. The method of claim 1, wherein the disease is an insect-borne disease.

11. The method of claim 10, wherein the disease is malaria, yellow fever, dengue fever, West Nile encephalitis, Rift Valley fever, Arboviral Encephalitides, filariasis, babesiosis, ehrlichiosis, Lyme disease, Rocky Mountain spotted fever, Southern tick-associated rash illness, tick typhus, tularemia, encephalitis, Leishmaniasis, Carrion's disease, sand fly fever, African sleeping sickness, Chagas disease, lice infestation, epidemic relapsing fever, trench fever, typhus fever, onchoceriasis, tularemia, anthrax, loiasis, yaws, conjunctivitis, dysentery, cholera, poliomyelitis, bubonic plague or murine typhus.

12. The method of claim 1, wherein the evening primrose oil is present in amount between approximately 4% and 6% w/w.

13. The method of claim 1, wherein the catnip oil is present in an amount between approximately 4% and 6% w/w.

14. The method of claim 1, wherein the composition further comprises an emulsifier.

15. The method of claim 1, wherein the composition further comprises an anti-microbial agent.

16. The method of claim 1, wherein the composition further comprises an antioxidant.

17. The method of claim 1, wherein the composition further comprises an emulsifier, an anti-microbial agent, and an antioxidant.

18. A method for repelling a target pest from a target area comprising applying a composition comprising evening primrose oil, catnip oil and a carrier to the target area, wherein the evening primrose oil is present in an amount between approximately 2% and 8% w/w, and the catnip oil is present in an amount between approximately 2% and 8% w/w.

19. The method of claim 18, wherein the target pest is at least one selected from the group consisting of biting, sucking and chewing insects.

20. The method of claim 18, wherein the target pest is a mosquito, house fly, barn fly, face fly, bush fly, black fly, no see'um, deer fly, horse fly, beetle, gnat, tick, beer bug, flea, louse, bed bug, earwig, ant, cockroach, aphid, spruce bud worm, corn borer, sandflea, tsetse fly, mite or assassin bug.

21. The method of claim 18, wherein the target area is at least one area on a human, animal, bird, plant, crop, tree, soil, field, greenhouse, barn, granary, home, deck, pool, commercial building, clothing, tent, shoe, boot, blanket, sleeping bag, backpack, table cloth or picnic table.

22. The method of claim 18, wherein the evening primrose oil is present in an amount between approximately 4% and 6% w/w.

23. The method of claim 18, wherein the catnip oil is present in an amount between approximately 4% and 6% w/w.

24. The method of claim 18, wherein the composition further comprises an emulsifier.

25. The method of claim 18, wherein the composition further comprises an anti-microbial agent.

26. The method of claim 18, wherein the composition further comprises an antioxidant.

27. The method of claim 18, wherein the composition further comprises one or more additional plant extract oils, wherein the one or more additional plant extract oil is allspice, anisum, basil, cajeput, cedar, chrysanthemum, cinnamon, citronella, clove, eucalyptus, garlic, geranium, lavender, marjoram, neem, pennyroyal, peppermint, pine, rosemary, sage, spearmint, thyme or any other members of the mint (Lamiaceae or Labiatae) family, tea-tree, vanilla, verbena or a combination thereof.

28. The method of claim 27, wherein the one or more additional plant extract oil is present in an amount between approximately 0.1% and 50% w/w.

29. The method of claim 27, wherein the one or more additional plant extract oil is present in an amount between approximately 1% and 10% w/w.

30. The method of claim 18, wherein the composition further comprises an emulsifier, an anti-microbial agent, and an antioxidant.

31. The method of claim 18, wherein the composition further comprises DEET.

* * * * *